US008546428B2

(12) United States Patent
Hegyi et al.

(10) Patent No.: US 8,546,428 B2
(45) Date of Patent: Oct. 1, 2013

(54) FUMARATE SALT OF (ALPHA S, BETA R)-6-BROMO-ALPHA-[2-(DIMETHYL-AMINO)ETHYL]-2-METHOXY-ALPHA-1-NAPHTHALENYL-BETA-PHENYL-3-QUINOLINEETHANOL

(75) Inventors: Jean François Alexandre Lucas Hegyi, Diest (BE); Wim Albert Alex Aelterman, Gierle (BE); Yolande Lydia Lang, Vosselaar (BE); Sigrid Carl Maria Stokbroekx, Beerse (BE); Carina Leys, Stabroek (BE); Peter Jozef Maria Van Remoortere, Kapellen (BE); Anne Faure, Vosselaar (BE)

(73) Assignee: Janssen Pharmaceutica NV, Beerse (BE)

( * ) Notice: Subject to any disclaimer, the term of this patent is extended or adjusted under 35 U.S.C. 154(b) by 472 days.

(21) Appl. No.: 12/515,986

(22) PCT Filed: Dec. 3, 2007

(86) PCT No.: PCT/EP2007/063186
§ 371 (c)(1),
(2), (4) Date: May 22, 2009

(87) PCT Pub. No.: WO2008/068231
PCT Pub. Date: Jun. 12, 2008

(65) Prior Publication Data
US 2010/0028428 A1    Feb. 4, 2010

(30) Foreign Application Priority Data
Dec. 5, 2006  (EP) ..................................... 06125443

(51) Int. Cl.
*A61K 31/04* (2006.01)
(52) U.S. Cl.
USPC ........................................... 514/312
(58) Field of Classification Search
USPC ......................................... 514/312; 546/159
See application file for complete search history.

(56) References Cited

U.S. PATENT DOCUMENTS 5,965,572 A     10/1999  Ellis et al.
7,498,343 B2 *   3/2009  Van Gestel et al. ........... 514/312

FOREIGN PATENT DOCUMENTS

WO   WO 2004/011436 A1   2/2004
WO   WO 2005/117875 A1   12/2005

OTHER PUBLICATIONS

Database Registry: XP002433954 Abstract (Accession No. 845533-86-0) May 14, 2005.
Martindale, The Extra Pharmacopoeia, Twenty-ninth Edition, Edited by James E. F. Reynolds, p. 1435-1436 (1989).

* cited by examiner

*Primary Examiner* — D M Seaman
(74) *Attorney, Agent, or Firm* — Thomas J. Dodd

(57) ABSTRACT

The present invention relates to the fumarate salt of (alpha S, beta R)-6-bromo-alpha-[2-(dimethylamino)ethyl]-2-methoxy-alpha-1-naphthalenyl-beta-phenyl-3-quinolineethanol, pharmaceutical compositions comprising as active ingredient said salt and to processes for their preparation.

12 Claims, No Drawings

FUMARATE SALT OF (ALPHA S, BETA R)-6-BROMO-ALPHA-[2-(DIMETHYLAMINO) ETHYL]-2-METHOXY-ALPHA-1-NAPHTHALENYL-BETA-PHENYL-3-QUINOLINEETHANOL

CROSS-REFERENCE TO RELATED APPLICATIONS

The present application claims the benefits of the filing of Application Nos. EP 06125443.9 filed Dec. 5, 2006, and PCT/EP2007/063186 filed Dec. 3, 2007. The complete disclosures of the aforementioned related patent applications are hereby incorporated herein by reference for all purposes.

The present invention relates to the fumarate salt of (alpha S, beta R)-6-bromo-alpha-[2-(dimethylamino)ethyl]-2-methoxy-alpha-1-naphthalenyl-beta-phenyl-3-quinolineethanol, in particular (alpha S, beta R)-6-bromo-alpha-[2-(dimethylamino)ethyl]-2-methoxy-alpha-1-naphthalenyl-beta-phenyl-3-quinolineethanol (2E)-2-butenedioate (1:1); to pharmaceutical compositions comprising said fumarate salt, to the preparation of the salt and the pharmaceutical compositions.

6-bromo-α-[2-(dimethylamino)ethyl]-2-methoxy-α-1-naphthalenyl-β-phenyl-3-quinolineethanol and stereoisomeric forms thereof are disclosed in WO2004/011436 as antimycobacterial agents useful for the treatment of mycobacterial diseases, particularly those diseases caused by pathogenic mycobacteria such as Mycobacterium (M.) tuberculosis, M. bovis, M. avium and M. marinum.

Enantiomer (alpha S, beta R)-6-bromo-α-[2-(dimethylamino)ethyl]-2-methoxy-α-1-naphthalenyl-α-phenyl-3-quinolineethanol corresponds to compound 12 (or the A1 enantiomer) of WO2004/011436 and is a preferred compound to treat mycobacterial diseases, in particular tuberculosis.

It was found that the fumarate salt of (alpha S, beta R)-6-bromo-alpha-[2-(dimethylamino)ethyl]-2-methoxy-alpha-1-naphthalenyl-beta-phenyl-3-quinolineethanol is non-hygroscopic and stable. Due to its solubility in water and its dissolution rate, a pharmaceutical composition comprising said salt can be obtained with an acceptable bioavailability.

Thus, the present invention relates to the fumarate salt of (alpha S, beta R)-6-bromo-alpha-[2-(dimethylamino)ethyl]-2-methoxy-alpha-1-naphthalenyl-beta-phenyl-3-quinolineethanol, in particular (alpha S, beta R)-6-bromo-alpha-[2-(dimethylamino) ethyl]-2-methoxy-alpha-1-naphthalenyl-beta-phenyl-3-quinolineethanol (2E)-2-butenedioate (1:1) represented by the following formula:

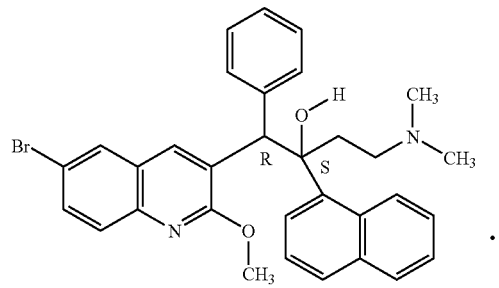

-continued

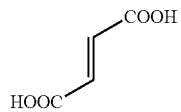

The fumarate salt of the present invention can be prepared by reacting the corresponding free base with fumaric acid in the presence of a suitable solvent, such as for example isopropanol.

The present salt shows activity against Mycobacteria including drug resistant strains, in particular Mycobacterium tuberculosis, M. bovis, M. avium, M. leprae and M. marinum, especially against Mycobacterium tuberculosis, including drug-resistant M. tuberculosis strains. The salt shows activity against active, sensitive, susceptible Mycobacteria strains and latent, dormant, persistent Mycobacteria strains.

The term "drug resistant" as used hereinbefore or hereinafter is a term well understood by the person skilled in microbiology. A drug resistant Mycobacterium is a Mycobacterium which is no longer susceptible to at least one previously effective drug; which has developed the ability to withstand antibiotic attack by at least one previously effective drug. A drug resistant strain may relay that ability to withstand to its progeny. Said resistance may be due to random genetic mutations in the bacterial cell that alters its sensitivity to a single drug or to different drugs.

MDR tuberculosis is a specific form of drug resistant tuberculosis due to a bacterium resistant to at least isoniazid and rifampicin (with or without resistance to other drugs), which are at present the two most powerful anti-TB drugs. Thus, whenever used hereinbefore or hereinafter "drug resistant" includes multi drug resistant.

Mycobacterium tuberculosis results in more than 2 million deaths per year and is the leading cause of mortality in people infected with HIV. In spite of decades of tuberculosis (TB) control programs, about 2 billion people are infected by M. tuberculosis, though asymptomatically. About 10% of these individuals are at risk of developing active TB during their lifespan. There is thus a high need for drugs to treat active TB.

The global epidemic of TB is fuelled by infection of HIV patients with TB and rise of multi-drug resistant TB strains (MDR-TB). The reactivation of latent TB is a high risk factor for disease development and accounts for 32% deaths in HIV infected individuals. To control TB epidemic, the need is to discover new drugs that can also kill dormant or latent bacilli. The dormant TB can get reactivated to cause disease by several factors like suppression of host immunity by use of immunosuppressive agents like antibodies against tumor necrosis factor α or interferon-γ. In case of HIV positive patients the only prophylactic treatment available for latent TB is two-three months regimens of rifampicin, pyrazinamide. The efficacy of the treatment regime is still not clear and furthermore the length of the treatments is an important constrain in resource-limited environments. Hence there is a drastic need to identify new drugs, which can act as chemoprophylatic agents for individuals harboring latent TB bacilli. The tubercle bacilli enter healthy individuals by inhalation; they are phagocytosed by the alveolar macrophages of the lungs. This leads to potent immune response and formation of granulomas, which consist of macrophages infected with M. tuberculosis surrounded by T cells. After a period of 6-8 weeks the host immune response cause death of infected cells by necrosis and accumulation of caseous material with certain extracellular bacilli, surrounded by macrophages, epitheloid cells and layers of lymphoid tissue at the periphery. In case of healthy individuals, most of the mycobacteria are killed in these environments but a small proportion of bacilli still survive and are thought to exist in a non-replicating, hypometabolic state and are tolerant to killing by anti-TB drugs like isoniazid. These bacilli can remain in the altered physiological environments even for individual's lifetime without showing any clinical symptoms of disease. However, in 10% of the cases these latent bacilli may reactivate to cause disease. One of the hypothesis about development of these persistent bacteria is patho-physiological environment in human lesions namely, reduced oxygen tension, nutrient limitation, and acidic pH. These factors have been postulated to render these bacteria phenotypically tolerant to major antimycobacterial drugs.

The antimycobacterial activity of the free base is described in WO 2004/011436, which is incorporated herein by reference.

Due to the antimycobacterial activity, the present compound is useful in the treatment of a mycobacterial infection. In general, the compound of the present invention may be useful in the treatment of warm-blooded mammals infected with mycobacteria. Therefore, the present compound can be used as a medicine. In particular, the compound of the present invention can be used as a medicine to treat or prevent a mycobacterial infection. Said use as a medicine or method of treatment comprises the administration to subjects infected with *Mycobacteria*, in particular with *Mycobacterium tuberculosis*, of an amount effective to combat the Mycobacterial infection. In particular, the present compound may be used in the manufacture of a medicament for the treatment or the prevention of a mycobacterial infection, preferably for the treatment of a *Mycobacterium tuberculosis* infection.

In view of the utility of the present compound, there is also provided a method of treating mammals, including humans, suffering from or a method of preventing warm-blooded mammals, including humans, to suffer from a mycobacterial infection, especially a *Mycobacterium tuberculosis* infection. Said method comprises the administration, preferably oral administration, of an effective amount of a salt of the present invention to mammals including humans.

Therefore, the present invention also relates to a pharmaceutical composition comprising a pharmaceutically acceptable carrier and as active ingredient a therapeutically effective amount of the fumarate salt of ($\alpha$S, $\beta$R)-6-bromo-$\alpha$-[2-(dimethylamino)ethyl]-2-methoxy-$\alpha$-1-naphthalenyl-$\beta$-phenyl-3-quinolineethanol, in particular (alpha S, beta R)-6-bromo-alpha-[2-(dimethylamino)ethyl]-2-methoxy-alpha-1-naphthalenyl-beta-phenyl-3-quinolineethanol (2E)-2-butenedioate (1:1).

The present compound may be formulated into various pharmaceutical compositions for administration purposes. As appropriate compositions there may be cited all compositions usually employed for systemically administering drugs. To prepare the pharmaceutical compositions of this invention, an effective amount of the present salt as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral unit dosage forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations, which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

The salt of the present invention may also be administered via inhalation or insufflation by means of methods and formulations employed in the art for administration via this way. Thus, in general the salt of the present invention may be administered to the lungs in the form of a solution, a suspension or a dry powder. Any system developed for the delivery of solutions, suspensions or dry powders via oral or nasal inhalation or insufflation are suitable for the administration of the present compound.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

The exact dosage and frequency of administration depends on the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

Preferably, the pharmaceutical compositions of the present invention contain those quantities of the present fumarate salt equivalent to from about 1 mg to about 1000 mg of the corresponding free base, more preferably from about 10 mg to about 750 mg of the corresponding free base, even more preferably from about 50 mg to about 500 mg of the corresponding free base, most preferred the present pharmaceutical compositions contain about 100 mg of the corresponding free base (base equivalent).

Depending on the mode of administration, the pharmaceutical composition will preferably comprise from 0.05 to 99% by weight, more preferably from 0.1 to 70% by weight, even more preferably from 0.1 to 50% by weight of the active ingredient, and, from 1 to 99.95% by weight, more preferably from 30 to 99.9% by weight, even more preferably from 50 to 99.9% by weight of a pharmaceutically acceptable carrier, all percentages being based on the total weight of the composition.

An interesting embodiment of the present invention concerns an oral pharmaceutical composition, i.e. a pharmaceutical composition suitable for oral administration, comprising a pharmaceutically acceptable carrier and as active ingredient a therapeutically effective amount of the present salt.

In particular, the oral pharmaceutical composition is a solid oral pharmaceutical composition, more in particular a tablet or a capsule, even more in particular a tablet. It was found that oral administration of the present salt in a solid dosage form to fed subjects resulted in a higher bioavailability when compared to administration to fasted subjects. In fed conditions the oral bioavailability from a solid dosage form was comparable to the bioavailability of an oral solution. Therefore, the oral solid dosage form is preferably administered to fed subjects.

As used hereinbefore or hereinafter, the term "about" in relation to a numerical value x means, for example, x±10%.

The particle size of the present fumarate salt is preferably less than 200 μm.

The pharmaceutical compositions of the present invention preferably comprise a wetting agent.

As for the wetting agent in the compositions of the invention, there may be used any of the physiologically tolerable wetting agent suitable for use in a pharmaceutical composition.

It is well-known in the art that a wetting agent is an amphiphilic compound; it contains polar, hydrophilic moieties as well as non-polar, hydrophobic moieties.

The terms "hydrophilic" or "hydrophobic" are relative terms.

The relative hydrophilicity or hydrophobicity of a wetting agent may be expressed by its hydrophilic-lipophilic balance value ("HLB value). Wetting agents with a lower HLB value are catagorized as being "hydrophobic" wetting agents whereas wetting agents with a higher HLB value are catagorized as being "hydrophilic" wetting agents. As a rule of thumb, wetting agents having a HLB value greater than about 10 are generally considered as being hydrophilic wetting agents; wetting agents having a HLB value lower than about 10 are generally considered as being hydrophobic wetting agents.

The present compositions preferably comprise a hydrophilic wetting agent. It should be appreciated that the HLB value of a wetting agent is only a rough guide to indicate the hydrophilicity/hydrophobicity of a wetting agent. The HLB value of a particular wetting agent may vary depending upon the method used to determine the HLB value; may vary depending on its commercial source; is subject to batch to batch variability. A person skilled in the art can readily identify hydrophilic wetting agents suitable for use in the pharmaceutical compositions of the present invention.

The wetting agent of the present invention can be an anionic, a cationic, a zwitterionic or a non-ionic wetting agent, the latter being preferred. The wetting agent of the present invention can also be a mixture of two or more wetting agents.

Suitable wetting agents for use in the compositions of the present invention are listed below. It should be emphasized that said list of wetting agents is only illustrative, representative and not exhaustive. Thus the invention is not limited to the wetting agents listed below. In the present compositions, also mixtures of wetting agents may be used.

Suitable wetting agents which may be used in the present invention comprise:

a) Polyethylene glycol fatty acid monoesters comprising esters of lauric acid, oleic acid, stearic acid, ricinoic acid and the like with PEG 6, 7, 8, 9, 10, 12, 15, 20, 25, 30, 32, 40, 45, 50, 55, 100, 200, 300, 400, 600 and the like, for instance PEG-6 laurate or stearate, PEG-7 oleate or laurate, PEG-8 laurate or oleate or stearate, PEG-9 oleate or stearate, PEG-10 laurate or oleate or stearate, PEG-12 laurate or oleate or stearate or ricinoleate, PEG-15 stearate or oleate, PEG-20 laurate or oleate or stearate, PEG-25 stearate, PEG-32 laurate or oleate or stearate, PEG-30 stearate, PEG-40 laurate or oleate or stearate, PEG-45 stearate, PEG-50 stearate, PEG-55 stearate, PEG-100 oleate or stearate, PEG-200 oleate, PEG-400 oleate, PEG-600 oleate; (the wetting agents belonging to this group are for instance known as Cithrol, Algon, Kessco, Lauridac, Mapeg, Cremophor, Emulgante, Nikkol, Myrj, Crodet, Albunol, Lactomul)

b) Polyethylene glycol fatty acid diesters comprising diesters of lauric acid, stearic acid, palmic acid, oleic acid and the like with PEG-8, 10, 12, 20, 32, 400 and the like, for instance PEG-8 dilaurate or distearate, PEG-10 dipalmitate, PEG-12 dilaurate or distearate or dioleate, PEG-20 dilaurate or distearate or dioleatePEG-32 dilaurate or distearate or dioleate, PEG-400 dioleate or distearate; (the wetting agents belonging to this group are for instance known as Mapeg, Polyalso, Kessco, Cithrol)

c) Polyethylene glycol fatty acid mono- and diester mixtures such as for example PEG 4-150 mono and dilaurate, PEG 4-150 mono and dioleate, PEG 4-150 mono and distearate and the like; (the wetting agents belonging to this group are for instance known as Kessco)

d) Polyethylene glycol glycerol fatty acid esters such as for instance PEG-20 glyceryl laurate or glyceryl stearate or glyceryl oleate, PEG-30 glyceryl laurate or glyceryl oleate, PEG-15 glyceryl laurate, PEG-40 glyceryl laurate and the like; (the wetting agents belonging to this group are for instance known as Tagat, Glycerox L, Capmul), e) Alcohol-oil transesterification products comprising esters of alcohols or polyalcohols such as glycerol, propylene glycol, ethylene glycol, polyethylene glycol, sorbitol, pentaerythritol and the like with natural and/or hydrogenated oils or oil-soluble vitamins such as castor oil, hydrogenated castor oil, vitamin A, vitamin D, vitamin E, vitamin K, an edible vegetable oil e.g. corn oil, olive oil, peanut oil, palm kernel oil, apricot kernel oil, almond oil and the like, such as PEG-20 castor oil or hydrogenated castor oil or corn glycerides or almond glycerides, PEG-23 castor oil, PEG-25 hydrogenated castor oil or trioleate, PEG-35 castor oil, PEG-30 castor oil or hydrogenated castor oil, PEG-38 castor oil, PEG-40 castor oil or hydrogenated castor oil or palm kernel oil, PEG-45 hydrogenated castor oil, PEG-50 castor oil or hydrogenated castor oil, PEG-56 castor oil, PEG-60 castor oil or hydrogenated castor oil or corn glycerides or almond glycerides, PEG-80 hydrogenated castor oil, PEG-100 castor oil or hydrogenated castor oil, PEG-200 castor oil, PEG-8 caprylic/capric glycerides, PEG-6 caprylic/capric glycerides, lauroyl macrogol-32 glyceride, stearoyl macrogol glyceride, tocopheryl PEG-1000 succinate (TPGS); (the wetting agents belonging to this group are for instance known as Emalex, Cremophor, Emulgante, Eumulgin, Nikkol, Thornley, Simulsol, Cerex, Crovol, Labrasol, Softigen, Gelucire, Vitamin E TPGS), f) polyglycerized fatty acids comprising polyglycerol esters of fatty acids such as for instance polyglyceryl-10 laurate or oleate or stearate, polyglyceryl-10 mono and dioleate, polyglyceryl polyricinoleate and the like; (the wetting agents belonging to this group are for instance known as Nikkol Decaglyn, Caprol or Polymuls)

g) Sterol derivatives comprising polyethylene glycol derivatives of sterol such as PEG-24 cholesterol ether, PEG-30 cholestanol, PEG-25 phyto sterol, PEG-30 soya sterol and the like; (the wetting agents belonging to this group are for instance known as Solulan™ or Nikkol BPSH)

h) Polyethylene glycol sorbitan fatty acid esters such as for example PEG-10 sorbitan laurate, PEG-20 sorbitan monolaurate or sorbitan tristearate or sorbitan monooleate or sorbitan trioleate or sorbitan monoisostearate or sorbitan monopalmiate or sorbitan monostearate, PEG-4 sorbitan monolaurate, PEG-5 sorbitan monooleate, PEG-6 sorbitan monooleate or sorbitan monolaurate or sorbitan monostearate, PEG-8 sorbitan monostearate, PEG-30 sorbitan tetraoleate, PEG-40 sorbitan oleate or sorbitan tetraoleate, PEG-60 sorbitan tetrastearate, PEG-80 sorbitan monolaurate, PEG sorbitol hexaoleate (Atlas G-1086) and the like; (the wetting agents belonging to this group are for instance known as Liposorb, Tween, Dacol MSS, Nikkol, Emalex, Atlas)

i) Polyethylene glycol alkyl ethers such as for instance PEG-10 oleyl ether or cetyl ether or stearyl ether, PEG-20 oleyl ether or cetyl ether or stearyl ether, PEG-9 lauryl ether, PEG-23 lauryl ether (laureth-23), PEG-100 stearyl ether and the like; (the wetting agents belonging to this group are for instance known as Volpo, Brij)

j) Sugar esters such as for instance sucrose distearate/monostearate, sucrose monostearate or monopalmitate or monolaurate and the like; (the wetting agents belonging to this group are for instance known as Sucro ester, Crodesta, Saccharose monolaurate)

k) Polyethylene glycol alkyl phenols such as for instance PEG-10-100 nonyl phenol (Triton X series), PEG-15-100 ocyl phenol ether (Triton N series) and the like;

l) Polyoxyethylene-polyoxypropylene block copolymers (poloxamers) such as for instance poloxamer 108, poloxamer 188, poloxamer 237, poloxamer 288 and the like; (the wetting agents belonging to this group are for instance known as Synperonic PE, Pluronic, Emkalyx, Lutrol™, Supronic, Monolan, Pluracare, Plurodac)

m) ionic wetting agents including cationic, anionic and zwitterionic surfactans such as the fatty acid salts e.g. sodium oleate, sodium lauryl sulfate, sodium lauryl sarcosinate, sodium dioctyl sulfosuccinate, sodium myristate, sodium palmitate, sodium state, sodium ricinoleate and the like; such as bile salts e.g. sodium cholate, sodium taurocholate, sodium glycocholate and the like; such as phospholipids e.g. egg/soy lecithin, hydroxylated lecithin, lysophosphatidylcholine, phosphatidylcholine, phosphatidyl ethanolamine, phosphatidyl glycerol, phosphatidyl serine and the like; such as phosphoric acid esters e.g. diethanolammonium polyoxyethylene-10 oleyl ether phosphate, esterification products of fatty alcohols or fatty alcohol ethoxylates with phosphoric acid or anhydride; such as carboxylates e.g. succinylated monoglycerides, sodium stearyl fumarate, stearoyl propylene glycol hydrogen succinate, mono/diacetylated tartaric acid esters of mono- and diglycerides, citric acid esters of mono- and diglycerides, glyceryl-lacto esters of fatty acids, lactylic esters of fatty acids, calcium/sodium stearoyl-2-lactylate, calcium/sodium stearoyl lactylate, alginate salts, propylene glycol alginate, ether carboxylates and the like; such as sulfates and sulfonates e.g. ethoxylated alkyl sulfates, alkyl benzene sulfates, alpha-olefin sulfonates, acyl isethionates, acyl taurates, alkyl glyceryl ether sulfonates, octyl sulfosuccinate disodium, disodium undecyleneamido-MEA-sulfosuccinate and the like; such as cationic wetting agents e.g. hexadecyl triammonium bromide, decyl trimethyl ammonium bromide, cetyl trimethyl ammonium bromide, dodecyl ammonium chloride, alkyl benzyldimethylammonium salts, diisobutyl phenoxyethoxydimethyl benzylammonium salts, alkylpyridinium salts, betaines (lauryl betaine), ethoxylated amines (polyoxyethylene-15 coconut amine) and the like.

When in the above list of suitable wetting agents, different possibilities are listed such as for example PEG-20 oleyl ether or cetyl ether or stearyl ether, this means that PEG-20 oleyl ether and PEG-20 cetyl ether and PEG-20 stearyl ether are intended. Thus for instance PEG-20 castor oil or hydrogenated castor oil or corn glycerides or almond glycerides has to be read as PEG-20 castor oil and PEG-20 hydrogenated castor oil and PEG-20 corn glycerides and PEG-20 almond glycerides.

Preferred wetting agents in the present compositions are those agents belonging to the group of the polyethylene glycol sorbitan fatty acid esters, such as wetting agents known as Tween, e.g. Tween 20, 60, 80. Most preferred, the wetting agent is Tween 20.

In the compositions of the invention, the wetting agent is preferably present at a concentration from about 0.01 to about 5% by weight relative to the total weight of the composition, preferably from about 0.1 to about 3% by weight, more preferably from about 0.1 to about 1% by weight.

The quantity of wetting agent used in the present compositions may depend on the amount of the compound present in the composition or on the particle size of the compound. A higher amount or a smaller particle size may require more wetting agent.

In case of a solid oral pharmaceutical composition according to the present invention, such as a tablet or a capsule, the composition may also further contain an organic polymer.

The organic polymer may be used as a binder during the manufacture of the composition.

The organic polymer used in the compositions of the invention may be any of the physiologically tolerable water soluble synthetic, semi-synthetic or non-synthetic organic polymers.

Thus for example the polymer may be a natural polymer such as a polysaccharide or polypeptide or a derivative thereof, or a synthetic polymer such as a polyalkylene oxide (e.g. PEG), polyacrylate, polyvinylpyrrolidone, etc. Mixed polymers, e.g. block copolymers and glycopeptides may of course also be used.

The polymer conveniently has a molecular weight in the range 500 D to 2 MD, and conveniently has an apparent viscosity of 1 to 15,000 mPa·s when in a 2% aqueous solution at 20° C. For example, the water-soluble polymer can be selected from the group comprising alkylcelluloses such as methylcellulose, hydroxyakylcelluloses such as hydroxymethylcellulose, hydroxyethylcellulose, hydroxypropylcellulose and hydroxybutylcellulose, hydroxyalkyl alkylcelluloses such as hydroxyethyl methylcellulose and hydroxypropyl methylcellulose, carboxyalkylcelluloses such as carboxymethylcellulose, alkali metal salts of carboxyalkylcelluloses such as sodium carboxymethylcellulose, carboxyalkylalkylcelluloses such as carboxymethylethylcellulose, carboxyalkylcellulose esters, starches, pectins such as sodium carboxymethylamylopectin, chitin derivates such as chitosan, heparin and heparinoids,
polysaccharides such as alginic acid, alkali metal and ammonium salts thereof, carrageenans, galactomannans, tragacanth, agar-agar, gum arabic, guargum and xanthan gum,
polyacrylic acids and the salts thereof,
polymethacrylic acids and the salts thereof, methacrylate copolymers,
polyvinylalcohol,
polyvinylpyrrolidone, copolymers of polyvinylpyrrolidone with vinyl acetate,
polyalkylene oxides such as polyethylene oxide and polypropylene oxide and copolymers of ethylene oxide and propylene oxide, e.g. poloxamers and poloxamines.

Non-enumerated polymers which are pharmaceutically acceptable and have appropriate physico-chemical properties as defined hereinbefore are equally suited for preparing compositions according to the present invention.

Preferably the organic polymer is starch, polyvinylpyrrolidone or a cellulose ether, e.g. PVP K29-32, PVP K90, methyl cellulose, hydroxypropylcellulose, hydroxyethyl methylcellulose, or hydroxypropyl methylcellulose (HPMC).

Said HPMC contains sufficient hydroxypropyl and methoxy groups to render it water-soluble. HPMC having a methoxy degree of substitution from about 0.8 to about 2.5 and a hydroxypropyl molar substitution from about 0.05 to about 3.0 are generally water-soluble. Methoxy degree of substitution refers to the average number of methyl ether groups present per anhydroglucose unit of the cellulose molecule. Hydroxy-propyl molar substitution refers to the average number of moles of propylene oxide which have reacted with each anhydroglucose unit of the cellulose molecule. A preferred HPMC is hypromellose 2910 15 mPa·s or hypromellose 2910 5 mPa·s, especially hypromellose 2910 15 mPa·s. Hydroxypropyl methylcellulose is the United States Adopted Name for hypromellose (see Martindale, The Extra Pharmacopoeia, 29th edition, page 1435). In the four digit number "2910", the first two digits represent the approximate percentage of methoxyl groups and the third and fourth digits the approximate percentage composition of hydroxypropoxyl groups; 15 mPa·s or 5 mPa·s is a value indicative of the apparent viscosity of a 2% aqueous solution at 20° C.

In the compositions of the invention the organic polymer may conveniently be present up to about 10% by weight, preferably from about 0.1 to about 5%, more preferably from about 0.5 to about 3% by weight (relative to the total weight of the composition).

In case of a solid oral pharmaceutical composition according to the present invention, such as a tablet or a capsule, the composition may also further contain a diluent and/or a glidant.

Pharmaceutical acceptable diluents comprise calcium carbonate, dibasic calcium phosphate, dibasic calcium phosphate dihydrate, tribasic calcium phosphate, calcium sulfate, microcrystalline cellulose including silicified microcrystalline cellulose, powdered cellulose, dextrates, dextrin, dextrose excipient, fructose, kaolin, lactitol, lactose anhydrous, lactose monohydrate, mannitol, sorbitol, starch, pregelatinized starch, sodium chloride, sucrose, compressible sugar, confectioner's sugar, a spray-dried mixture of lactose monohydrate and microcrystalline cellulose (75:25), commercially available as Microcelac®, a co-processed spray-dried mixture of microcrystalline cellulose and colloidal silicon dioxide (98:2), commercially available as Prosolv®. Preferred is lactose monohydrate, especially 200 mesh, microcrystalline cellulose or maize starch.

Pharmaceutically acceptable glidants comprise talc, colloidal silicon dioxide, starch. magnesium stearate. Preferred is colloidal silicon dioxide.

In case of a tablet, the composition may also further comprise a disintegrant and a lubricant.

Pharmaceutically acceptable disintegrants comprise starch, ion exchange resins, e.g. Amberlite, cross-linked polyvinylpyrrolidone, modified cellulose gum, e.g. croscarmellose sodium (e.g. Ac-di-Sol®), sodium starch glycollate, sodium carboxymethylcellulose, sodium dodecyl sulphate, modified corn starch, microcrystalline cellulose, magnesium aluminium silicate, alginic acid, alginate, powdered cellulose.

Pharmaceutically acceptable lubricants comprise magnesium stearate, calcium stearate, stearic acid, talc, polyethylene glycol, sodium lauryl sulfate, magnesium lauryl sulphate.

Tablets of the present invention may in addition include other optional excipients such as, for example, flavors, sweeteners and colors.

Solid pharmaceutical compositions according to the present invention may comprise by weight based on the total weight of the composition:
(a) from 5 to 50% of the present fumarate salt;
(b) from 0.01 to 5% of a wetting agent;
(c) from 40 to 92% of a diluent;
(d) from 0.1 to 5% of a glidant.

Tablets according to the present invention may comprise by weight based on the total weight of the tablet core:
(a) from 5 to 50% of the present fumarate salt;
(b) from 0.01 to 5% of a wetting agent;
(c) from 40 to 92% of a diluent;
(d) from 0 to 10% of a polymer;
(e) from 2 to 10% of a disintegrant;
(f) from 0.1 to 5% of a glidant;
(g) from 0.1 to 1.5% of a lubricant.

Tablets of the present invention may optionally be film-coated following art-known coating procedures. Film-coated tablets are easier to swallow than uncoated tablet cores, are usually easier to distinguish from other tablets—in particular when the film-coat contains a dye or a pigment—, may have reduced tackiness, and may furthermore have an improved stability (increased shelf-life), e.g. because the coating may protect the active ingredient from the influence of light. Preferably, the film coat is an immediate release coat. Film coatings may comprise a film-forming polymer and optionally a plasticizer or a pigment. An example of a suitable film-forming polymer is hydroxypropyl methylcellulose, and an example of a suitable plasticizer is polyethyleneglycol, e.g. macrogol 3000 or 6000, or triacetin. Commercially available suitable coatings for pharmaceutical tablets are well-known to a person skilled in the art. Preferably, the film coating is a non-transparant film coating. An example of a suitable coating is Opadry®, in particular coating powder Opadry® II White.

Tablets of the present invention can be prepared by direct compression or wet granulation.

Therefore, the present invention also concerns a process of preparing a tablet comprising the present fumarate salt comprising the steps of:
(i) dry blending the active ingredient, the disintegrant and the optional glidant with the diluent;
(ii) optionally mixing the lubricant with the mixture obtained in step (i);
(iii) compressing the mixture obtained in step (i) or in step (ii) in the dry state into a tablet; and
(iv) optionally film-coating the tablet obtained in step (iii).

The present invention also concerns a process of preparing a tablet comprising the present fumarate salt comprising the steps of:
(i) dry blending the active ingredient and part of the diluent;
(ii) preparing a granulation solution optionally containing the binder and wetting agent;
(iii) spraying the granulation solution obtained in step (ii) on the mixture obtained in step (i);
(iv) drying the wet granulate obtained in step (iii) followed by sieving and optionally mixing;
(v) mixing the remaining part of the diluent, the disintegrant, the optional glidant and optionally the binder and wetting agent in the mixture obtained in step (iv);
(vi) optionally adding the lubricant to the mixture obtained in step (v);
(vii) compressing the mixture obtained in step (vi) into a tablet;
(viii) optionally film-coating the tablet obtained in step (vii).

The present invention also concerns a process of preparing a tablet comprising the present fumarate salt comprising the steps of:
(i) dry blending the active ingredient and part of the diluent;
(ii) preparing a binder solution by dissolving the binder and the wetting agent in the binder solution solvent;
(iii) spraying the binder solution obtained in step (ii) on the mixture obtained in step (i);
(iv) drying the wet granulate obtained in step (iii) followed by sieving and optionally mixing;
(v) mixing the remaining part of the diluent, the disintegrant and the optional glidant in the mixture obtained in step (iv);
(vi) optionally adding the lubricant to the mixture obtained in step (v);
(vii) compressing the mixture obtained in step (vi) into a tablet;
(viii) optionally film-coating the tablet obtained in step (vii).

A person skilled in the art will recognize the most appropriate equipment to be used for the above-described processes.

The above general route of preparing tablets of the present invention may be modified by a person skilled in the art by for instance adding certain ingredients at other stages than indicated above.

EXPERIMENTAL PART

A. Synthesis of the fumarate salt of (αS,βR)-6-bromo-α-[2-(dimethylamino)ethyl]-2-methoxy-α-1-naphthalenyl-β-phenyl-3-quinolineethanol 10 g (0.018 mol) of (αS,βR)-6-bromo-α-[2-(dimethylamino)ethyl]-2-methoxy-α-1-naphthalenyl-β-phenyl-3-quinolineethanol and 2.13 g (0.018 mol) of fumaric acid were suspended in 185 ml isopropanol. Dicalite (0.25 g) and charcoal (0.25 g) were added to the suspension. The mixture was refluxed for an hour, the reaction mixture was cooled to 70° C. and filtered in the heat. The filter cake was washed with 10 ml isopropanol. The mother liquor was slowly cooled to 50° C. and stirred for 1 hour at this temperature. The reaction mixture was further cooled to room temperature and stirred for 16 hours. The crystals were filtered off and washed with 20 ml isopropanol. The wet cake was dried at 50° C. during 16 hours.

Yield: 10 g of (alpha S, beta R)-6-bromo-alpha-[2-(dimethylamino)ethyl]-2-methoxy-alpha-1-naphthalenyl-beta-phenyl-3-quinolineethanol (2E)-2-butenedioate (1:1) (white solid) (82%).

B. Tablet Formulation

Tablet composition illustrating the present invention:

| Present fumarate salt | 120.89 mg (i.e. 100 mg base equivalent) |
|---|---|
| Lactose monohydrate (200 mesh) | 152.91 mg |
| Maize starch | 66 mg |
| Hypromellose 2910 15 mPa·s | 8 mg |
| Polysorbate 20 | 1 mg |
| Microcrystalline cellulose | 82.2 mg |
| Croscarmellose sodium | 23 mg |
| Colloidal silicon dioxide | 1.4 mg |
| Magnesium stearate | 4.6 mg |

The above tablets were prepared by dissolving hypromellose and polysorbate 20 in purified water (q.s.) followed by spraying said solution on fluidized powder consisting of a mixture of the fumarate salt, lactose monohydrate and maize starch. The obtained granulate was dried, sieved and mixed with microcrystalline cellulose, croscarmellose sodium and colloidal silicon dioxide. After addition of magnesium stearate, the powder mixture was compressed into tablets.

Said tablets may further optionally be film coated with a suspension of Coating powder Opadry® II White in purified water.

C. Capsule Formulation

| Present fumarate salt | 60.445 | mg |
|---|---|---|
| Lactose monohydrate (200 mesh) | 298.555 | mg |
| Polysorbate 20 | 1 | mg |
| Purified water | 9 | µl* |
| Capsule size 0 red cap red body | 1 | PC |

*= Solvent used during the manufacturing of the powder mixture but eliminated at the end of the process, so not present in the capsules.

The invention claimed is:
1. A solid pharmaceutical composition comprising a pharmaceutically acceptable carrier and as active ingredient a therapeutically effective amount of the Fumarate salt of (alpha S, beta R)-6-bromo-alpha-[2-(dimethylamino)ethyl]-2-methoxy-alpha-1-naphthalenyl-beta-phenyl-3-quinolineethanol, and further comprising a wetting agent, said wetting agent being a polyethylene glycol sorbitan fatty acid ester.

2. A pharmaceutical composition according to claim 1 wherein the composition is suitable for oral administration.

3. A pharmaceutical composition according to claim 1 comprising by weight based on the total weight of the composition:
(a) from 5 to 50% of active ingredient;
(b) from 0.01 to 5% of a said wetting agent;
(c) from 40 to 92% of a diluent;
(d) from 0.1 to 5% of a glidant.

4. A pharmaceutical composition according to claim 1 wherein the composition is in the form of a tablet.

5. A pharmaceutical composition according to claim 4 comprising by weight based on the total weight of the tablet core
(a) from 5 to 50% of active ingredient;
(b) from 0.01 to 5% of a wetting agent;
(c) from 40 to 92% of a diluent;
(d) from 0 to 10% of a polymer;
(e) from 2 to 10% of a disintegrant;

(f) from 0.1 to 5% of a glidant;
(g) from 0.1 to 1.5% of a lubricant.

6. A pharmaceutical composition according to claim 5 having the following composition

| Active ingredient | 120.89 mg (i.e. 100 mg base equivalent) |
|---|---|
| Lactose monohydrate (200 mesh) | 152.91 mg |
| Maize starch | 66 mg |
| Hypromellose 2910 15 mPa·s | 8 mg |
| Polysorbate 20 | 1 mg |
| Microcrystalline cellulose | 82.2 mg |
| Croscarmellose sodium | 23 mg |
| Colloidal silicon dioxide | 1.4 mg |
| Magnesium stearate | 4.6 mg. |

7. A pharmaceutical composition according to claim 4 which is film-coated.

8. A process for preparing a pharmaceutical composition according to claim 4 comprising the following steps:
   (i) dry blending the active ingredient and part of the diluent;
   (ii) preparing a binder solution by dissolving the binder and the wetting agent in the binder solution solvent;
   (iii) spraying the binder solution obtained in step (ii) on the mixture obtained in step (i);
   (iv) drying the wet powder obtained in step (iii) followed by sieving and optionally mixing;
   (v) mixing the remaining part of the diluent, the disintegrant and the optional glidant in the mixture obtained in step (iv);
   (vi) optionally adding the lubricant to the mixture obtained in step (v);
   (vii) compressing the mixture obtained in step (vi) into a tablet;
   (viii) optionally film-coating the tablet obtained in step (vii).

9. A process for preparing a pharmaceutical composition according to claim 4 comprising the following steps:
   (i) dry blending the active ingredient and part of the diluent;
   (ii) preparing a granulation solution optionally containing the binder and wetting agent;
   (iii) spraying the granulation solution obtained in step (ii) on the mixture obtained in step (i);
   (iv) drying the wet granulate obtained in step (iii) followed by sieving and optionally mixing;
   (v) mixing the remaining part of the diluent, the disintegrant, the optional glidant and optionally the binder and wetting agent in the mixture obtained in step (iv);
   (vi) optionally adding the lubricant to the mixture obtained in step (v);
   (vii) compressing the mixture obtained in step (vi) into a tablet;
   (viii) optionally film-coating the tablet obtained in step (vii).

10. Process for the preparation of a compound as claimed in claim 1 characterized by reacting the corresponding free base with fumaric acid in the presence of a suitable solvent.

11. A method for treating a patient suffering from a mycobacterial infection, said method comprising administering to said patient a therapeutically effective amount of the composition of claim 1.

12. The method of claim 11 wherein the Patient is suffering from tuberculosis.

* * * * *